(12) United States Patent
Zebala

(10) Patent No.: US 7,235,660 B1
(45) Date of Patent: Jun. 26, 2007

(54) FACILE PROCESS FOR THE PREPARATION OF HIGH-PURITY AMINOPTERIN

(76) Inventor: John A. Zebala, 215 Clay St. NW. Suite B-5, Auburn, WA (US) 98001

( * ) Notice: Subject to any disclaimer, the term of this patent is extended or adjusted under 35 U.S.C. 154(b) by 0 days.

(21) Appl. No.: 11/619,102

(22) Filed: Jan. 2, 2007

(51) Int. Cl.
*C07D 475/00* (2006.01)
*C07D 475/08* (2006.01)
(52) U.S. Cl. .................................... 544/260
(58) Field of Classification Search ................. 544/260
See application file for complete search history.

(56) References Cited

U.S. PATENT DOCUMENTS 4,767,859 A    8/1988    Zimmermann

*Primary Examiner*—Shaojia Anna Jiang
*Assistant Examiner*—Cecilia Jaisle
(74) *Attorney, Agent, or Firm*—Joseph Cagno

(57) ABSTRACT

A process for the preparation of aminopterin with a purity greater than 90%, which comprises reacting folic acid, with a silazane in an organic solvent at a temperature from 60 to 180° C., the said solvent being a tertiary amine organic solvent, or, if a catalyst which is acid in nature is present, a basic organic solvent or acetonitrile, and further adding water such that there is about 2.8 to 7.0 mole water for each mole of folic acid.

18 Claims, No Drawings

FACILE PROCESS FOR THE PREPARATION OF HIGH-PURITY AMINOPTERIN

BACKGROUND

It is known from U.S. Pat. No. 4,767,859 a process for the preparation of aminopterin from folic acid by the direct amination of the pteridine ring of folic acid. Generally, the process is a method for the preparation of aminopterin which comprises reacting folic acid with a silazane in an organic solvent at a temperature from 60 to 180° C., the said solvent being a tertiary amine organic solvent, or, if a catalyst which is acid in nature is present, a basic organic solvent or acetonitrile, and in the absence of ammonia.

In one embodiment, the method describes the use of anhydrous pyridine in a 17 hour reaction at 100° C. to obtain 79% pure aminopterin. In another embodiment, the method describes the use of anhydrous pyridine in a 48 hour reaction at 100° C. to obtain 33.3% pure aminopterin. This level of purity is inadequate for the commercial production of pharmaceutical grade aminopterin.

DETAILED DESCRIPTION OF THE INVENTION

It has now been found in a surprising and unexpected way that the addition of a critical amount of water to the process described in U.S. Pat. No. 4,767,859 has a profound effect on increasing the purity of aminopterin obtained. Because folic acid and pyridine are hygroscopic and absorb variable amounts of water depending on the environment, the amount of water in the reaction cannot be discerned from the prior art with any certainty and further is an unpredictable quantity.

The methodology of U.S. Pat. No. 4,767,859 is incorporated herein by reference for all purposes. In particular, a process for the preparation of aminopterin (N-[4-{N-[(2,4-diamino-6-pteridinyl)methyl]amino}benzoyl]-L-(+)-glutamic acid) from folic acid.

Folic acid can be aminated by treatment with a silazane so as to replace a hydroxy radical by an amino radical without affecting the rest of the molecule. The process gives aminopterin of a purity greater than about 90%, without the need to use ammonia or to operate under high pressure.

The process is generally carried out by heating folic acid with a silazane such as hexamethyldisilazane.

The reaction is carried out in a basic organic solvent or, if an acidic catalyst is present, in a basic solvent or in acetonitrile.

A tertiary amine such as pyridine, N,N-dimethylaniline or quinoline is generally used as the basic organic solvent. It is particularly advantageous to use pyridine.

Further, water is added such that there is about 2.8 to 7.0 mole water for each mole of folic acid.

When the process is carried out in the presence of a catalyst which is acid in nature, it is particularly advantageous to use as the catalyst an inorganic or organic acid such as hydrochloric, sulfuric, formic or p-toluenesulfonic acid, or a salt which is acid in nature, obtained from an acid and a weaker base, such as an organic or inorganic ammonium salt, e.g. ammonium chloride, sulfate or formate, pyridinium hydrochloride, pyridinium p-toluenesulfonate or N-methylanilinium trifluoroacetate. It is also possible to use a Lewis acid such as zinc chloride as the acid catalyst.

When such a catalyst is present, the reaction is advantageously effected in the presence of a basic organic solvent such as pyridine or of acetonitrile.

Pyridinium p-toluenesulfonate in acetonitrile is of very particular value.

The silazane is generally used at a rate of 2 to 10 moles per mole of folic acid.

When the process is carried out in the presence of p-toluenesulfonic acid, 0.01 to 0.2 mole of catalyst per mole of folic acid is generally used.

The reaction temperature is generally between 60° C. and 180° C. and the reaction is complete after heating for 15 to 25 hours at this temperature.

Aminopterin may be separated from the reaction mixture by the usual extraction technique and may advantageously be isolated in the form of a metal salt such as the sodium salt.

In one embodiment, a process is provided for the preparation of aminopterin with a purity greater than about 90%, which comprises reacting folic acid, with a silazane in an organic solvent at a temperature from 60 to 180° C., the said solvent being a tertiary amine organic solvent, or, if a catalyst which is acid in nature is present, a basic organic solvent or acetonitrile, and further adding water such that there is about 2.8 to 7.0 mole, and more preferably 2.8 to 3.2 mole of water, and most preferably about 3.0 mole of water for each mole of folic acid.

The purity of aminopterin obtained in this embodiment is preferably greater than about 90%, 93%, and more preferably greater than about 95% and 98%.

EXAMPLES

A stainless steel reactor was charged with 3.6 g folic acid dihydrate (0.0075 mole)), 0.25 g p-tolulenesulfonic acid monohydrate, and 29.5 g anhydrous pyridine. A Karl-Fischer titration analysis was performed to determine and control for the water content of this mixture. A water content of 1.08% was found (0.3601 g). To this mixture was then added 16 g hexamethyldisilazane (0.099 mole), and the vessel was then purged with Argon and then tightly sealed. An amount of water was then added as described in Table I for each example.

After 20-24 hrs at 110° C. (internal pressure of approximately 20 psi), the reaction mixture was cooled to room temperature and then the reactor was opened. The contents were transferred to a 500 mL round-bottom flask. Two 30 mL washings of acetonitrile were used to aid in the transfer. The excess reagents and solvent were removed by rotary evaporation at 40-45° C. under vacuum. To the residue, 150 mL water was added and the pH adjusted to approximately 9 with 10% sodium hydroxide solution. Then the solution was filtered to remove any insolubles. The filtrate was acidified with glacial acetic acid to a pH of approximately 4. The solid that precipitated was filtered using a Buchner funnel (a slow filtration). The solid was then washed twice with 10 mL of water. The wet cake was submitted for HPLC analysis, and the purity as reported in Table I for each example.

TABLE I

| Example | Water from Karl-Fisher (g) | Water Added (g) | Total Water (g) | Moles Water to Moles Folic Acid | % Aminopterin Purity | % Folic Acid | % Unknown Impurity |
|---|---|---|---|---|---|---|---|
| 1* | 0.3601 | 0.000 | 0.3602 | 2.67 | 23.4 | 0.1 | 69.3, 5.2 |
| 2 | 0.3601 | 0.070 | 0.4301 | 3.19 | 96.9 | 0.0 | 3.1 |
| 3 | 0.3601 | 0.145 | 0.5052 | 3.74 | 93.6 | 0.885 | 3.3, 2.0 |
| 4 | 0.3601 | 0.440 | 0.8002 | 5.93 | 95.3 | | |
| 5 | 0.3601 | 0.600 | 0.9602 | 7.11 | 92.9 | | |
| 6* | 0.3601 | 1.500 | 1.8602 | 13.78 | 4.5 | 73.8 | |

*Not a method of the subject invention.

In Example 7 of the invention, the same procedure as in Example 2 was performed, except that activated charcol was added after the pH was adjusted to approximately 9. In this case, the purity of aminopterin obtained was 99%. Other methods of further purifying will be known to those in the art; for example through the formation of the magnesium salt as described by Ti Li Loo (Ti Li Loo, The purificaton of aminopterin, J. Med. Chem. 8:139, 1965).

What is claimed is:

1. A process for the preparation of aminopterin with a purity greater than about 90%, which comprises reacting folic acid, with a silazane in an organic solvent at a temperature from 60 to 180° C., the said solvent being a tertiary amine organic solvent, or, if a catalyst which is acid in nature is present, a basic organic solvent or acetonitrile, and adding water such that there is about 2.8 to 7.0 mole water for each mole of folic acid.

2. Process according to claim 1, wherein the purity is greater than about 93%.

3. Process according to claim 1, wherein the purity is greater than about 95%.

4. Process according to claim 1, wherein the purity is greater than about 98%.

5. Process according to claim 1, wherein the silazane used is hexamethyldisilazane.

6. Process according to claim 1, wherein 5 to 15 moles of silazane are used per mole of folic acid.

7. Process according to claim 1, wherein the basic organic solvent used is pyridine, N,N-dimethylaniline or quinoline.

8. Process according to claim 1, wherein the aminopterin is isolated as a metal salt.

9. Process according to claim 1, wherein the reaction is carried out in the presence of a catalyst which is acid in nature in a basic organic solvent or in acetonitrile.

10. Process according to claim 9, wherein the catalyst is an inorganic or organic acid, an organic or inorganic ammonium salt or a Lewis acid.

11. Process according to claim 9, wherein the catalyst is ammonium chloride, sulfate or formate, pyridinium p-toluenesulfonate or hydrochloride or N-methylanilinium trifluoroacetate.

12. Process according to claim 9, wherein the acidic catalyst is pyridinium p-toluenesulfonate and the solvent is acetonitrile.

13. A process for the preparation of aminopterin with a purity greater than 90%, which comprises reacting folic acid, with a silazane in an organic solvent at a temperature from 60 to 180° C., the said solvent being a tertiary amine organic solvent, or, if a catalyst which is acid in nature is present, a basic organic solvent or acetonitrile, wherein the improvement consists of adding water such that there is about 2.8 to 7.0 mole water for each mole of folic acid.

14. A process according to claim 13, wherein there is about 2.8 to 3.2 mole water for each mole of folic acid.

15. A process according to claim 13, wherein there is about 3.0 mole water for each mole of folic acid.

16. Process according to claim 13, wherein the purity is greater than about 93%.

17. Process according to claim 13, wherein the purity is greater than about 95%.

18. Process according to claim 13, wherein the purity is greater than about 98%.

* * * * *